United States Patent
Agrawal et al.

(10) Patent No.: US 10,835,729 B2
(45) Date of Patent: Nov. 17, 2020

(54) HEMOSTASIS VALVE DESIGN FOR INTRODUCER SHEATH

(71) Applicant: BOSTON SCIENTIFIC LIMITED, Hamilton (BM)

(72) Inventors: Sumit Agrawal, Gurgaon (IN); Henry J. Pepin, Loretto, MN (US); Somashekar Reddy, New Delhi/Gurgaon (IN)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 294 days.

(21) Appl. No.: 15/806,315

(22) Filed: Nov. 7, 2017

(65) Prior Publication Data

US 2018/0126142 A1    May 10, 2018

Related U.S. Application Data

(60) Provisional application No. 62/419,670, filed on Nov. 9, 2016.

(51) Int. Cl.
    *A61M 39/06*     (2006.01)
    *A61M 25/00*     (2006.01)

(52) U.S. Cl.
CPC ........ *A61M 39/06* (2013.01); *A61M 25/0097* (2013.01); *A61M 39/0606* (2013.01); *A61M 2025/0098* (2013.01); *A61M 2039/062* (2013.01); *A61M 2039/064* (2013.01); *A61M 2039/066* (2013.01); *A61M 2039/068* (2013.01); *A61M 2039/0626* (2013.01)

(58) Field of Classification Search
CPC ...... A61M 39/00; A61M 39/02; A61M 39/22; A61M 2025/0098; A61M 2039/062; A61M 2039/0626; A61M 2039/064; A61M 2039/066; A61M 2039/068; A61M 25/0097; A61M 39/06; A61M 39/0606
USPC .................................................. 604/167.04
See application file for complete search history.

(56) References Cited

U.S. PATENT DOCUMENTS

| | | |
|---|---|---|
| 5,092,857 A | 3/1992 | Fleishhacker |
| 5,935,112 A | 8/1999 | Stevens et al. |
| 6,086,570 A | 7/2000 | Aboul-Hosn et al. |
| 6,702,255 B2 | 3/2004 | Dehdashtian |
| 8,371,555 B2 | 2/2013 | Rickerd et al. |
| 9,108,032 B2 | 8/2015 | Melsheimer |

(Continued)

FOREIGN PATENT DOCUMENTS

| | | |
|---|---|---|
| EP | 2404638 A1 | 1/2012 |
| EP | 3037126 A1 | 6/2016 |

(Continued)

OTHER PUBLICATIONS

International Search Report and Written Opinion for Application No. PCT/US2017/060479, 14 pages, dated Jan. 30, 2018.

*Primary Examiner* — Jason E Flick
(74) *Attorney, Agent, or Firm* — Seager, Tufte & Wickhem LLP

(57) ABSTRACT

A hemostasis valve for use in a medical device. The hemostasis valve may include a generally cylindrical body having a proximal side, a distal side, and a thickness extending therebetween. The proximal side may include a tapered central region having a surface sloped towards a center of the body and the distal side may include a distally extending curved central region.

16 Claims, 7 Drawing Sheets

(56) References Cited

U.S. PATENT DOCUMENTS

| | | |
|---|---|---|
| 9,439,751 B2 | 9/2016 | White et al. |
| 2005/0010238 A1 | 1/2005 | Potter et al. |
| 2006/0145116 A1 | 7/2006 | Rickerd et al. |
| 2009/0012476 A1 | 1/2009 | Catlin |
| 2010/0312190 A1 | 12/2010 | Searfoss et al. |
| 2012/0065676 A1 | 3/2012 | Hadba et al. |
| 2013/0310765 A1* | 11/2013 | Stephens ........... A61M 25/0668 604/246 |
| 2014/0039263 A1 | 2/2014 | Le |
| 2014/0277340 A1 | 9/2014 | White et al. |
| 2016/0175576 A1* | 6/2016 | Neff ................. A61M 39/0613 604/167.03 |
| 2016/0338867 A1 | 11/2016 | White et al. |
| 2018/0126142 A1 | 5/2018 | Agrawal et al. |

FOREIGN PATENT DOCUMENTS

| | | |
|---|---|---|
| JP | 09047512 A | 2/1997 |
| JP | 10500345 A | 1/1998 |
| JP | 10127775 A | 5/1998 |
| JP | 2015205219 A | 11/2015 |
| WO | 9534341 A1 | 12/1995 |

* cited by examiner

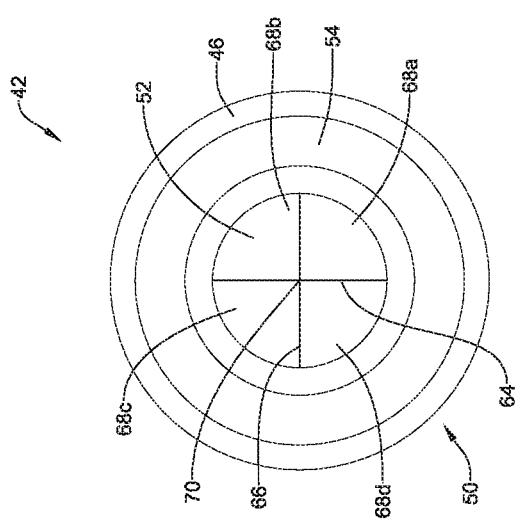

HEMOSTASIS VALVE DESIGN FOR INTRODUCER SHEATH

CROSS REFERENCE TO RELATED APPLICATIONS

This application claims the benefit of U.S. Provisional Patent Application Ser. No. 62/419,670 filed on Nov. 9, 2016, the disclosure of which is incorporated herein by reference.

TECHNICAL FIELD

The disclosure is directed to a hemostasis valve. More particularly, the disclosure is directed to a self-centering hemostasis valve.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing methods, and use alternatives for medical devices.

In a first example, a hemostasis valve for use in a medical device may comprise a generally cylindrical body designed to be disposed within a hub body of a medical device. The body may have a proximal side and a distal side. The proximal side may include a tapered central region having a surface sloped towards a diametrical center of the body and the distal side may include a distally extending curved central region.

Alternatively or additionally to any of the examples above, in another example, the body may comprise an elastomeric silicone.

Alternatively or additionally to any of the examples above, in another example, the body may comprise a liquid silicone rubber (LSR).

Alternatively or additionally to any of the examples above, in another example, the body may comprise an enhanced tear resistant (ETR) silicone elastomer.

Alternatively or additionally to any of the examples above, in another example, the hemostasis valve may further comprise one or more slits formed in the body and extending at least partially through the body between the tapered central region and the curved central region of the body.

Alternatively or additionally to any of the examples above, in another example, the one or more slits may be formed in a cross slit thru (CST) configuration.

Alternatively or additionally to any of the examples above, in another example, the one or more slits may be formed in cross slit partial (CSP) configuration.

Alternatively or additionally to any of the examples above, in another example, the one or more slits may be formed in a star slit thru (SST) configuration.

Alternatively or additionally to any of the examples above, in another example, wherein the tapered central region may be configured to guide a supplemental medical device to the diametrical center of the body.

Alternatively or additionally to any of the examples above, in another example, the body may further comprise a flanged outer perimeter, the flanged outer perimeter configured to engage a hub body of a hemostasis valve assembly.

In another example, a hemostasis valve assembly may comprise a hub body defining a cavity, a strain relief portion extending distally from the hub body, an end cap coupled to a distal end of the hub body, and a hemostasis valve positioned within the cavity of the hub body and coupled between the hub body and the end cap. The hemostasis valve may comprise a generally cylindrical valve body having a proximal side including a tapered central region having a surface sloped towards a diametrical center of the body and a distal side including a distally extending curved central region.

Alternatively or additionally to any of the examples above, in another example, the valve body may comprise an elastomeric silicone.

Alternatively or additionally to any of the examples above, in another example, the valve body may comprise a liquid silicone rubber (LSR).

Alternatively or additionally to any of the examples above, in another example, the valve body may comprise an enhanced tear resistant (ETR) silicone elastomer.

Alternatively or additionally to any of the examples above, in another example, the hemostasis valve assembly may further comprise one or more slits formed in the valve body and extending at least partially through the valve body between the tapered central region and the curved central region.

In another example, a hemostasis valve for use in a medical device may comprise a generally cylindrical body designed to be disposed within a hub body of a medical device. The body may have a proximal side and a distal side. The proximal side may include a tapered central region having a surface sloped towards a diametrical center of the body and the distal side may include a distally extending curved central region.

Alternatively or additionally to any of the examples above, in another example, the body may comprise an elastomeric silicone.

Alternatively or additionally to any of the examples above, in another example, the body may comprise a liquid silicone rubber (LSR).

Alternatively or additionally to any of the examples above, in another example, the body may comprise an enhanced tear resistant (ETR) silicone elastomer.

Alternatively or additionally to any of the examples above, in another example, the hemostasis valve may further comprise one or more slits formed in the body and extending at least partially through the body between the tapered central region and the curved central region of the body.

Alternatively or additionally to any of the examples above, in another example, the one or more slits may be formed in a cross slit thru (CST) configuration.

Alternatively or additionally to any of the examples above, in another example, the one or more slits may be formed in cross slit partial (CSP) configuration.

Alternatively or additionally to any of the examples above, in another example, the one or more slits may be formed in a star slit thru (SST) configuration.

Alternatively or additionally to any of the examples above, in another example, the tapered central region may be configured to guide a supplemental medical device to the diametrical center of the body.

Alternatively or additionally to any of the examples above, in another example, the body may further comprise a flanged outer perimeter, the flanged outer perimeter configured to engage a hub body of a hemostasis valve assembly.

In another example a hemostasis valve assembly may comprise a hub body defining a cavity, a strain relief portion extending distally from the hub body, an end cap coupled to a distal end of the hub body, and a hemostasis valve positioned within the cavity of the hub body and coupled between the hub body and the end cap. The hemostasis valve may comprise a generally cylindrical valve body having a proximal side including a tapered central region having a surface sloped towards a diametrical center of the body and a distal side including a distally extending curved central region.

Alternatively or additionally to any of the examples above, in another example, the valve body may comprise an elastomeric silicone.

Alternatively or additionally to any of the examples above, in another example, the valve body may comprise a liquid silicone rubber (LSR).

Alternatively or additionally to any of the examples above, in another example, the valve body may comprise an enhanced tear resistant (ETR) silicone elastomer.

Alternatively or additionally to any of the examples above, in another example, the hemostasis valve assembly may further comprise one or more slits formed in the valve body and extending at least partially through the valve body between the tapered central region and the curved central region.

Alternatively or additionally to any of the examples above, in another example, the valve body may further comprise a flanged outer perimeter, the flanged outer perimeter configured to engage an interlocking groove in the hub body.

Alternatively or additionally to any of the examples above, in another example, the valve body may further comprise a first annular groove formed in the proximal side and a second annular groove formed in the distal side, the first annular groove configured to engage an interlocking feature in the end cap and the second annular groove configured to engage an interlocking feature in the hub body.

Alternatively or additionally to any of the examples above, in another example, the tapered central region may be configured to guide a medical device to the diametrical center of the valve body.

In another example a hemostasis valve assembly may comprise a hub body defining a cavity, a strain relief portion extending distally from the hub body, an end cap coupled to a distal end of the hub body, and a hemostasis valve positioned within the cavity of the hub body and coupled between the hub body and the end cap. The hemostasis valve may comprise a generally cylindrical elastomeric valve body having a proximal side and a distal side, a tapered central region having a surface sloped towards a diametrical center of the valve body on the proximal side thereof, a distally extending curved central region on the distal side thereof, a first annular groove formed in the proximal side, a second annular groove formed in the distal side, and a flanged outer perimeter.

Alternatively or additionally to any of the examples above, in another example, the hemostasis valve may further comprise one or more slits formed in the valve body and extending at least partially through the valve body between the tapered central region and the curved central region.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 6A is a proximal end view of the illustrative hemostasis valve of FIG. 3 having a slit configuration.

Figure 1:
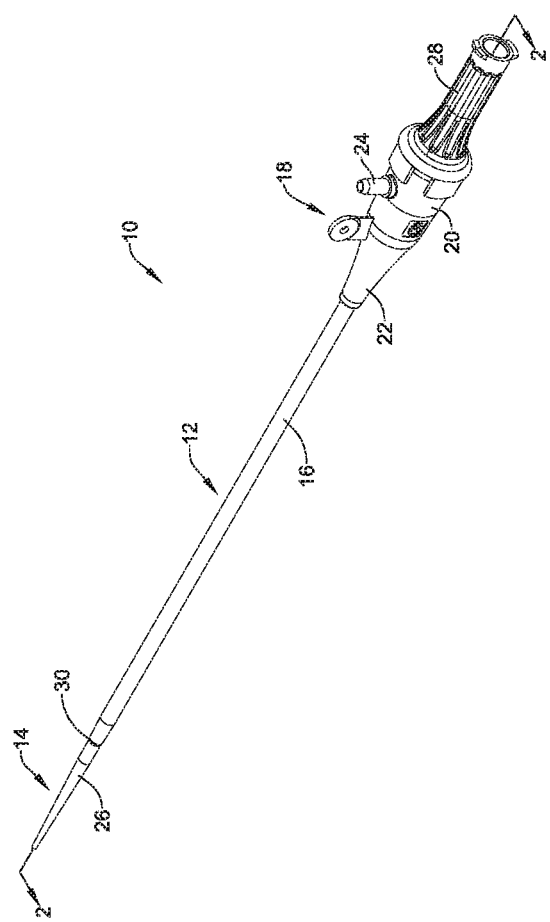
FIG. 1 is a perspective view of an illustrative vascular access system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

FIG. 1 is a perspective view of an illustrative vascular access system 10. The vascular access system 10 may be used to gain vessel access during a diagnostic or interventional procedure. While the system 10 is described in terms of vascular access, the system 10 may be used to access other parts of the body. The access system 10 may include an introducer sheath 12 and a dilator 14. The introducer sheath 12 includes an elongate shaft 16 and a hemostasis valve assembly 18. As will be described in more detail herein, the hemostasis valve assembly 18 may include a valve member or gasket which reduces or prevents blood loss when the introducer sheath 12 is inserted into a vessel while allowing for the passage of other devices (e.g., dilators, guide catheters, etc.) through the introducer sheath 12.

In some cases, the distal tip 30 of the elongate shaft 16 may be tapered to facilitate smooth insertion into the vascular system and/or to provide a smooth transition to the dilator 14. The elongate shaft 16 of the introducer sheath 12 may have a size (outside diameter or profile) ranging from 4 French (F) to 9F, and a length ranging from 10 centimeters (cm) to 25 cm. However, the outer diameter can be smaller than 4F or greater than 9F. It is further contemplated that the length of the shaft 16 may be shorter than 10 cm or longer than 25 cm. The hemostasis valve assembly 18 may include a hub body 20 and a strain relief portion 22 coupled to or formed as a unitary structure with the hub body 20 and extending distally therefrom. The hub body 20 may include a side port 24 for connection to a flush or injection tube subassembly (not explicitly shown). The dilator 14 includes an elongate shaft 26 and a handle 28. It should be understood that the hemostasis valve assembly 18, or the components thereof, may be used with other medical devices, such as, but not limited to interventional catheters, diagnostic catheters, guide sheaths, etc.

Figure 2:
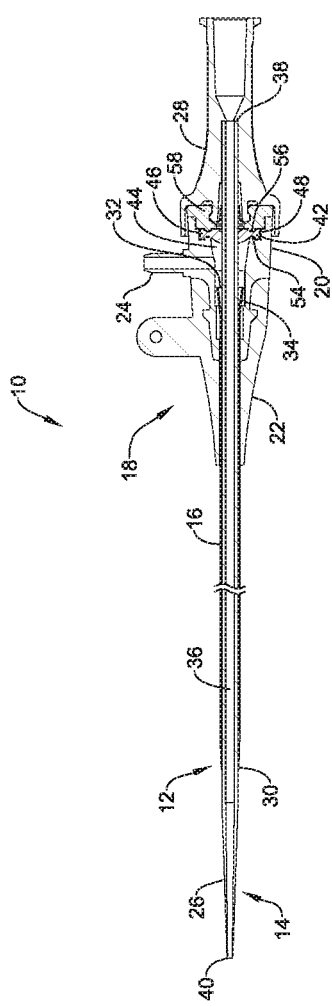
FIG. 2 is a cross-sectional view of the illustrative vascular access system of FIG. 1, taken at line 2-2.

FIG. 2 is a cross-sectional view of the illustrative vascular access system 10 of FIG. 1, taken at line 2-2 in FIG. 1. The introducer sheath 12 includes a lumen 32 extending from a proximal end 34 to the distal tip 30 of the elongate shaft 16. The lumen 32 may be sized to receive the dilator 14, or other device. The hemostasis valve assembly 18 is connected to the proximal end 34 of the shaft 16 utilizing conventional techniques. The dilator 14 includes a lumen 36 extending from the proximal end 38 to the distal end 40 of the elongate shaft 26. The lumen 36 may be configured to receive a diagnostic or interventional device or therapy. The handle 28 may be connected to the proximal end 38 of the elongate shaft 26 of the dilator 14 using conventional techniques.

Figure 3:
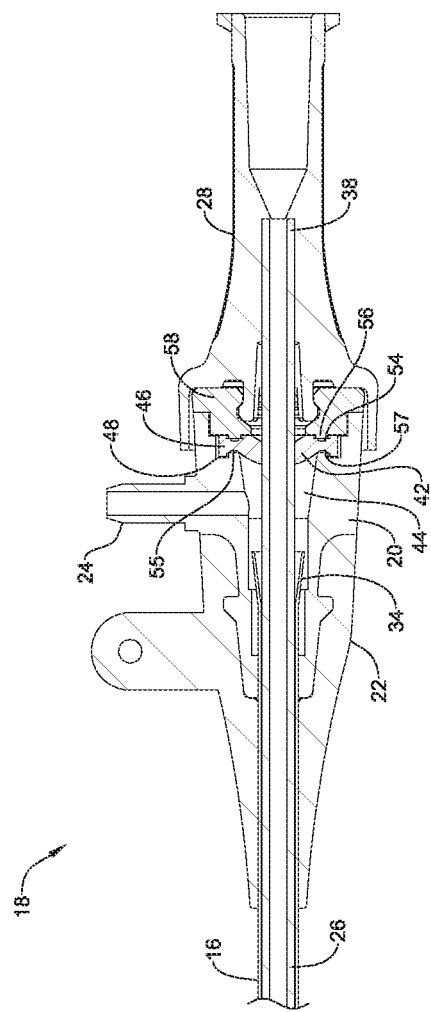
FIG. 3 is an enlarged cross-sectional view of the illustrative hemostasis valve assembly of FIG. 2.

Referring additionally to FIG. 3, which illustrates an enlarged cross-sectional view of the hemostasis valve assembly 18 of FIG. 2, a hemostasis valve or gasket 42 is positioned within a cavity 44 of the hub body 20 of the hemostasis valve assembly 18. The hemostasis valve 42 may include one or more interlocking features configured to engage mating features on the hub body 20 to retain the hemostasis valve in a desired position and/or orientation within the hub body 20 (e.g., at a fixed longitudinal and/or axial position within the cavity 44). For example, the hemostasis valve 42 may include a flanged outer perimeter 46 configured to be received in a mating recess or groove 48 in the hub body 20. The flanged outer perimeter 46 may have an increased thickness (e.g., in the proximal to distal direction, as shown in FIG. 3) relative to a pair of annular grooves or recesses 54, 55 formed in the proximal and distal end surfaces of the hemostasis valve 42. It is contemplated that the hemostasis valve 42 may be assembled within the cavity 44 of the hub body 20 prior to assembly with an end cap 58 of the hemostasis valve assembly 18. The end cap 58 may include a protrusion 56 configured to engage the annular groove 54 of the hemostasis valve 42. The second annular groove 55 may be configured to engage mating features, such as, but not limited to, a protrusion 57. The end cap 58 may frictionally or interlockingly secure the flanged outer perimeter 46 within the groove 48 and the annular grooves 54, 55 between the mating protrusions 56, 57.

During use (e.g., assembly of the dilator 14 with the introducer sheath 12), the distal end 40 of the dilator 14 is advanced distally (e.g., from a proximal side to a distal side of the hemostasis valve 42) through one or more slits in the hemostasis valve 42. The slits may be arranged to allow the hemostasis valve 42 to flex in the center, as described in more detail herein. In order to reduce the force necessary to advance the dilator 14 through the hemostasis valve 42, it may be desirable for the dilator 14 to pass through the center of hemostasis valve 42.

Figure 4:
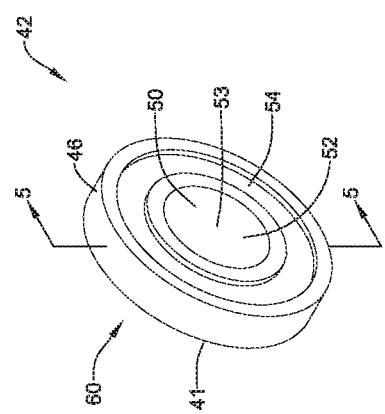
FIG. 4 is a perspective view of an illustrative hemostasis valve.

FIG. 4 illustrates a perspective view of the illustrative hemostasis valve 42. The hemostasis valve 42 may have a generally cylindrical, puck-like body 41 having a proximal side 50 and a distal side 60. The hemostasis valve 42 may be formed from an elastomeric silicone or other compliant material which allows the hemostasis valve 42 to resume its original shape after temporary deformation (e.g., an applied stress or force less than the yield point or fracture point). Some illustrative materials may include, but are not limited to, a liquid silicone rubber (LSR) elastomer or enhanced tear resistant (ETR) silicone elastomers.

The proximal side 50 of the hemostasis valve 42 may include a tapered or conical central region 52 with the surface sloped towards the center of the hemostasis valve 42. The tapered central region 52 decreases in diameter from the proximal side 50 towards the distal side 60 of the hemostasis valve 42. The tapered central region 52 may guide the distal end 40 of the dilator 14 towards a diametrical center 53 of the hemostasis valve 42. The tapered central region 52 may act as a self-centering mechanism which automatically guides the distal end 40 of the dilator 14 (or other supplemental medical device) towards the diametrical center 53 of the hemostasis valve 42 as it is assembled with the introducer sheath 12. The self-centering mechanism may facilitate device preparation before a procedure by reducing the force required to push the dilator 14 through the hemostasis valve 42 and/or reduce the number of attempts necessary to pass the dilator through the hemostasis valve 42.

Figure 5:
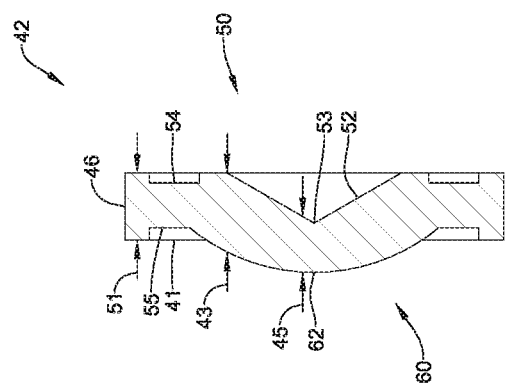
FIG. 5 is a cross-sectional view of the illustrative hemostasis valve of FIG. 3, taken at line 5-5 in FIG. 4.

FIG. 5 illustrates a cross-sectional view of the hemostasis valve 42, taken at line 5-5 in FIG. 4. The distal side 60 of the hemostasis valve 42 may include a distally extending curved or convex central region 62. The curvature of the curved central region 62 may help close the hemostasis valve 42 when blood, or other fluid, pushes against the distal side 60 of the hemostasis valve 42. It is contemplated that increasing or decreasing the curvature of the curved central region 62 may alter the effectiveness of the closure of the hemostasis valve 42.

As described herein, the flanged outer perimeter 46 may have an increased thickness 51 relative to a pair of annular grooves or recesses 54, 55 formed in the proximal and distal end surfaces of the hemostasis valve 42. The flanged outer perimeter 46 may be thicker 51 than other portions of the hemostasis valve 42 across the diameter thereof in order provide greater securement within the cavity 44 of the hub body 20. The thickness of the hemostasis valve 42 may vary across the diameter thereof. For example, a thickness 43 adjacent to the annular grooves 54, 55 may be greater than a thickness 45 adjacent to the diametrical center 53 of the hemostasis valve 42. It is contemplated reducing the thickness of the hemostasis valve 42 adjacent to the center 53 may reduce the force required to advance a device through the hemostasis valve 42. In some cases, the thickness 51 of the flanged outer perimeter 46 may be the same as, similar to, or different from the other thicknesses 43, 45 of the hemostasis valve 42, as desired. Other variations in the thickness(es) 43, 45, 51 of the hemostasis valve 42 are also contemplated. It is contemplated that changes in thickness may occur in a step-wise, or abrupt, manner or in a gradual, or smooth, manner, as desired. In some cases, the thickness may be uniform across the diameter of the hemostasis valve 42.

FIG. 6A illustrates a proximal end view of the hemostasis valve 42 having a slit configuration. The tapered central region 52 of the body 41 may include a vertical slit 64 and a horizontal slit 66 extending generally perpendicular to the vertical slit 64. The slits 64, 66 may both extend entirely through the thickness of the hemostasis valve 42 from the proximal side 50 to the distal side 60 (e.g., in a cross slit thru (CST) configuration). Alternatively, the vertical slit 64 may be formed in the proximal side 50 of the hemostasis valve 42 and extend distally partially through the thickness 45 between the tapered central region 52 and the curved central region 62. In such an instance, the horizontal slit 66 may be formed in the distal side 60 of the hemostasis valve 42 and extend proximally partially through the thickness 45 between the tapered central region 52 and the curved central region 62. The slits 64, 66 may meet between the tapered central region 52 and the curved central region 62 of the hemostasis valve 42 at their intersection point 70 to define an opening extending entirely through the thickness of the hemostasis valve 42 (e.g., in a cross slit partial (CSP) configuration). In some cases, the intersection point 70 may be at the diametrical center of the hemostasis valve 42, although this is not required The reverse configuration is also contemplated in which the horizontal slit 66 is formed in the proximal side 50 of the hemostasis valve 42 and extends distally partially through the thickness 45 between the tapered central region 52 and the curved central region 62 and the vertical slit 64 is formed in the distal side 60 of the hemostasis valve 42 and extends proximally partially through the thickness 45 between the tapered central region 52 and the curved central region 62. Other slit variations are also contemplated. For example a first slit may extend through the thickness 45 between the tapered central region 52 and the curved central region 62 while another slit may extend partially through the thickness 45 between the tapered central region 52 and the curved central region 62.

The slits 64, 66 may intersect at the intersection point 70 to define four flaps 68a, 68b, 68c, 68d (collectively, 68). The number and orientation of slits 64, 66 may be varied to vary a number of flaps 68, as desired. While the slits 64, 66 are described and shown as extending in a horizontal and vertical orientation, it is contemplated that the slits 64, 66 may be rotated such that the slits 64, 66 are offset from the horizontal and vertical axes. It is further contemplated that the slits 64, 66 may not necessarily intersect at a 90° angle. The intersection angle may be varied to create flaps 68 of varying size (e.g., two smaller and two larger). The flaps 68 may bend or flex in the distal direction as the dilator 14 is passed through the hemostasis valve 42. Once distal movement of the dilator 14 is ceased (and the distal biasing force is removed from the hemostasis valve 42), the curved central region 62 of the distal side 60 may bias the flaps 68 proximally, causing the flaps 68 to seal around an outer surface of the dilator 14 as well as bringing the flaps 68 into intimate contact adjacent to the slits 64, 66.

Figure 6B:
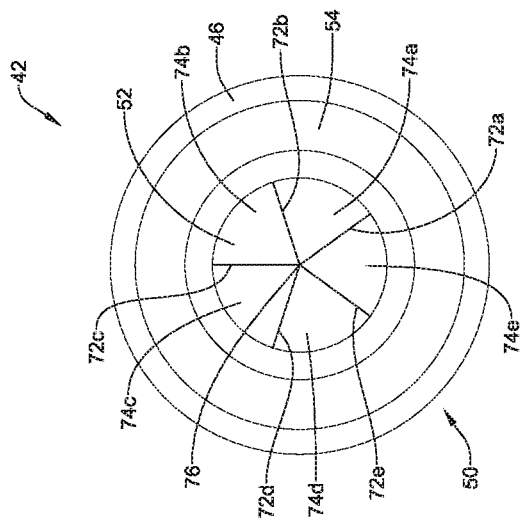
FIG. 6B is a proximal end view of the illustrative hemostasis valve of FIG. 3 having an alternative slit configuration.

FIG. 6B illustrates a proximal end view of the hemostasis valve 42 having an alternative slit configuration. The tapered central region 52 of the body 41 may include a plurality of slits 72a, 72b, 72c, 72d, 72e (collectively, 72). The slits 72 may be evenly distributed about the tapered central region 52. For example, in the illustrated embodiments, the slits 72 may be spaced approximately 72° from one another. It is contemplated that the slits 72 may also be distributed at irregular intervals (e.g., not evenly spaced), as desired. The slits 72 may extend entirely through the thickness of the hemostasis valve 42 between the tapered central region 52 and the curved central region 62 from the proximal side 50 to the distal side 60 (e.g., in a star slit thru (SST) configuration). In some embodiments, one or more of the slits 72 may extend partially through the thickness of the hemostasis valve 42 between the tapered central region 52 and the curved central region 62 from either proximal side 50 or the distal side 60 thereof. It is contemplated that all of the slits 72 may extend entirely through the thickness of the hemostasis valve 42 between the tapered central region 52 and the curved central region 62, all of the slits 72 may extend partially through the thickness of the hemostasis valve 42 between the tapered central region 52 and the curved central region 62 (from either the proximal side 50, the distal side 60, or combinations thereof), or the slits 72 may be a combination of slits that extend entirely or partially through the thickness of the hemostasis valve 42 between the tapered central region 52 and the curved central region 62.

The slits 72 may intersect at an intersection point 76 to define five flaps 74a, 74b, 74c, 74d, 74e (collectively, 74). The number and orientation of slits 72 may be varied to vary a number of flaps 74, as desired. As described herein, the slits 72 may not necessarily intersect at a 72° angle. The intersection angles may be varied to create flaps 74 of varying size. The flaps 74 may bend or flex in the distal direction as the dilator 14 is passed through the hemostasis valve 42. Once distal movement of the dilator 14 is ceased (and the distal biasing force is removed from the hemostasis valve 42), the curved central region 62 of the distal side 60 may bias the flaps 74 proximally causing the flaps 74 to seal around an outer surface of the dilator 14 as well as bringing the flaps 74 into intimate contact adjacent to the slits 72.

The materials that can be used for the various components of the medical devices and/or systems 10, 12, 14, 18, 42 (and/or other systems disclosed herein) and the various elements thereof disclosed herein may include those commonly associated with medical devices. For simplicity purposes, the following discussion makes reference to the system 10. However, this is not intended to limit the devices and methods described herein, as the discussion may be applied to other elements, members, components, or devices disclosed herein, such as, but not limited to, the elongate shafts 16, 26 and the hemostasis valve assembly 18, and/or elements or components thereof.

In some embodiments, the system 10, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of system 10, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, system 10, and/or components or portions thereof, may be made of a material that does not substantially distort the image and create substantial artifacts (e.g., gaps in the image). Certain ferromagnetic materials, for example, may not be suitable because they may create artifacts in an MRI image. The system 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, an exterior surface of the medical device system 10 (including, for example, an exterior surface of the delivery system) may be sandblasted, bead-blasted, sodium bicarbonate-blasted, electropolished, etc. In these as well as in some other embodiments, a coating, for example a lubricious, a hydrophilic, a protective, or other type of coating may be applied over portions or all of the outer sheath, or in embodiments without an outer sheath over portions of the delivery system, or other portions of the medical device system 10. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A hemostasis valve for use in a medical device, the hemostasis valve comprising:
a generally cylindrical body designed to be disposed within a hub body of a medical device, the body having a proximal side and a distal side;
wherein the proximal side includes a tapered central region having a proximal surface defining a cone with straight sides sloped towards a diametrical center point of the body;
wherein the distal side includes a distally extending curved central region having a curved distal surface, wherein the central region of the distal surface has a shape that is different from a shape of the central region of the proximal surface; and
wherein the body includes one or more slits formed in the body and extending at least partially through the body between the tapered central region and the curved central region of the body, wherein the one or more slits include at least a first slit and a second slit, wherein the first and second slits are formed in cross slit partial (CSP) configuration, with the first slit formed in the proximal side and extending distally only partially through the body and the second slit formed in the distal side and extending proximally only partially through the body, wherein the first and second slits meet between the proximal and distal sides at an intersection point defining an opening extending entirely through the body.

2. The hemostasis valve of claim 1, wherein the body comprises an elastomeric silicone.

3. The hemostasis valve of claim 1, wherein the body comprises a liquid silicone rubber (LSR).

4. The hemostasis valve of claim 1, wherein the body comprises an enhanced tear resistant (ETR) silicone elastomer.

5. The hemostasis valve of claim 1, wherein the one or more slits are formed in a cross slit thru (CST) configuration.

6. The hemostasis valve of claim 1, wherein the one or more slits are formed in a star slit thru (SST) configuration.

7. The hemostasis valve of claim 1, wherein the straight sides of the cone defined by the proximal surface of the body extend from a first end at the diametrical center point of the body radially outward to a second end, wherein the tapered central region has a thickness measured between the proximal side and distal side that decreases from the second end of the straight sides to the diametrical center point.

8. The hemostasis valve of claim 1, wherein the body further comprises a flanged outer perimeter, the flanged outer perimeter configured to engage a hub body of a hemostasis valve assembly.

9. A hemostasis valve assembly, comprising:
a hub body defining a cavity;
a strain relief portion extending distally from the hub body;
an end cap coupled to a proximal end of the hub body; and
a hemostasis valve positioned within the cavity of the hub body and coupled between the hub body and the end cap;
wherein the hemostasis valve comprises a generally cylindrical valve body having a proximal side including a tapered central region having a conical proximal surface sloped towards a diametrical center point of the body and a distal side including a distally extending curved central region having a curved distal surface, wherein the central region of the distal surface has a shape that is different from a shape of the central region of the proximal surface, wherein the valve body includes one or more slits formed in the valve body and extending at least partially through the valve body between the tapered central region and the curved central region, wherein the one or more slits include at least a first slit and a second slit, wherein the first and second slits are formed in cross slit partial (CSP) configuration, with the first slit formed in the proximal side and extending distally only partially through the valve body and the second slit formed in the distal side and extending proximally only partially through the valve body, wherein the first and second slits meet between the proximal and distal sides at an intersection point defining an opening extending entirely through the valve body.

10. The hemostasis valve assembly of claim 9, wherein the valve body comprises an elastomeric silicone.

11. The hemostasis valve assembly of claim 9, wherein the valve body comprises a liquid silicone rubber (LSR).

12. The hemostasis valve assembly of claim 9, wherein the valve body comprises an enhanced tear resistant (ETR) silicone elastomer.

13. The hemostasis valve assembly of claim 9, wherein the valve body further comprises a flanged outer perimeter, the flanged outer perimeter configured to engage an interlocking groove in the hub body.

14. The hemostasis valve assembly of claim 9, wherein the valve body further comprises a first annular groove formed in the proximal side and a second annular groove formed in the distal side, the first annular groove configured to engage an interlocking feature in the end cap and the second annular groove configured to engage an interlocking feature in the hub body.

15. The hemostasis valve assembly of claim 9, wherein the conical proximal surface of the valve body is defined by straight sides extending from a first end at the diametrical center point of the valve body radially outward to a second end, wherein the tapered central region has a thickness measured between the proximal side and distal side that decreases from the second end of the straight sides to the diametrical center point.

16. A hemostasis valve assembly, comprising:
a hub body defining a cavity;
a strain relief portion extending distally from the hub body;
an end cap coupled to a proximal end of the hub body; and
a hemostasis valve positioned within the cavity of the hub body and coupled between the hub body and the end cap, the hemostasis valve comprising:
a generally cylindrical elastomeric valve body having a proximal side and a distal side;
a tapered central region having a proximal surface sloped towards a diametrical center point of the valve body on the proximal side thereof;
a distally extending curved central region having a curved distal surface on the distal side thereof, wherein the central region of the distal surface has a shape that is different from a shape of the central region of the proximal surface;
a first annular groove formed in the proximal side;
a second annular groove formed in the distal side;
a flanged outer perimeter; and
one or more slits formed in the valve body and extending at least partially through the valve body between the tapered central region and the curved central region, wherein the one or more slits include at least a first slit and a second slit, wherein the first and second slits are formed in cross slit partial (CSP) configuration, with the first slit formed in the proximal side and extending distally only partially through the valve body and the second slit formed in the distal side and extending proximally only partially through the valve body, wherein the first and second slits meet between the proximal and distal sides at an intersection point defining an opening extending entirely through the valve body.

* * * * *